US011571504B2

(12) United States Patent
Radwanski et al.

(10) Patent No.: US 11,571,504 B2
(45) Date of Patent: Feb. 7, 2023

(54) APPARATUS AND METHOD FOR BATCH PHOTOACTIVATION OF MONONUCLEAR CELLS

(71) Applicant: Fenwal, Inc., Lake Zurich, IL (US)

(72) Inventors: Katherine N. Radwanski, Highland Park, IL (US); Lan T Nguyen, Vernon Hills, IL (US)

(73) Assignee: Fenwal, Inc., Lake Zurich, IL (US)

( * ) Notice: Subject to any disclaimer, the term of this patent is extended or adjusted under 35 U.S.C. 154(b) by 872 days.

(21) Appl. No.: 16/360,725

(22) Filed: Mar. 21, 2019

(65) Prior Publication Data
US 2020/0297914 A1 Sep. 24, 2020

(51) Int. Cl.
A61M 1/36 (2006.01)
(52) U.S. Cl.
CPC ........ *A61M 1/3683* (2014.02); *A61M 1/3644* (2014.02)
(58) Field of Classification Search
CPC .............. A61M 1/3681; A61M 1/3683; A61M 1/3686; A61M 1/3644; A61M 1/3496; A61M 1/362; A61M 1/3616; A61M 1/3675; A61M 1/302
See application file for complete search history.

(56) References Cited

U.S. PATENT DOCUMENTS

| 10,088,492 | B2* | 10/2018 | Wegener | A61M 1/3693 |
| 2005/0274672 | A1* | 12/2005 | Tu | A61M 1/26 210/645 |
| 2015/0283318 | A1* | 10/2015 | Wang | A61B 18/20 210/638 |
| 2019/0060549 | A1* | 2/2019 | Peritt | B04B 5/10 |

FOREIGN PATENT DOCUMENTS

EP 0239256 A1 9/1987

OTHER PUBLICATIONS

Extended European Search Report, counterpart EP Appl No. 20162789.0, dated Jul. 31, 2020.

* cited by examiner

Primary Examiner — Philip R Wiest
(74) Attorney, Agent, or Firm — Cook Alex Ltd.

(57) ABSTRACT

An apparatus and method for the batch photoactivation of mononuclear cells (MNCs) is described. The system includes a programmable controller configured to automatically separate whole blood in a first collection cycle to obtain a first quantity of MNCs; separate whole blood in a second collection cycle to obtain a second quantity of MNCs while simultaneously photoactivating the first quantity of MNCs to obtain a first quantity of treated MNCs; either store the first quantity of treated MNCs or reinfuse the first quantity of treated MNCs; photoactivate the second quantity of MNCs to obtain a second quantity of treated MNCs; either store the second quantity of treated MNCs or reinfuse the second quantity of treated MNCs; and reinfuse any blood components remaining after the second collection cycle.

13 Claims, 4 Drawing Sheets

APPARATUS AND METHOD FOR BATCH PHOTOACTIVATION OF MONONUCLEAR CELLS

FIELD OF THE DISCLOSURE

The present disclosure relates to an apparatus and methods for providing mononuclear cells that have been treated by extracorporeal photopheresis ("ECP"). More particularly, the present disclosure relates to apparatus and methods for providing batch photoactivation of mononuclear cells resulting in two or more therapeutic quantities of ECP-treated mononuclear cells from a single collection procedure.

BACKGROUND

Whole blood is made up of various cellular and non-cellular components such as red cells, white cells and platelets suspended in its liquid component, plasma. The administration of blood and/or blood components is common in the treatment of patients suffering from disease. Rather than infuse whole blood, it is more typical that individual components be administered to the patient as his or her needs require. For example, administration (infusion) of platelets is often prescribed for cancer patients whose ability to make platelets has been compromised by chemotherapy. Infusion of white blood cells (e.g. mononuclear cells), after the cells have undergone some additional processing or treatment, for example, to activate the mononuclear cells, may also be prescribed for therapeutic reasons including treatment of diseases that may involve the white blood cells. Thus, it is often desirable to separate and collect the desired blood component from whole blood and then treat the patient with the specific blood component. The remaining components may be returned to the donor or retained for other uses.

There are several diseases or disorders which are believed to primarily involve mononuclear cells, such as cutaneous T-cell lymphoma, organ allograft rejection after transplantation, graft versus host disease and autoimmune diseases such as rheumatoid arthritis, systemic sclerosis, among others, as described below.

Cutaneous T-cell lymphoma (CTCL) is a term that is used to describe a wide variety of disorders. Generally, CTCL is a type of cancer of the immune system where T-cells (a type of mononuclear cell) mutate or grow in an uncontrolled way, migrate to the skin and form itchy, scaly plaques or patches. More advanced stages of the disease also affect the lymph nodes. Therapeutic treatment options for CTCL have previously been limited. While chemotherapy has been utilized, this particular form of treatment also has many associated undesirable side effects such as lowered resistance to infection, bleeding, bruising, nausea, infertility and hair loss, just to name a few.

Organ allograft rejection may be characterized as the rejection of tissues that are foreign to a host, including transplanted cardiac tissue as well as lung, liver and renal transplants. Immunosuppression drug therapy following transplantation is common. However, there are potential drawbacks including recurring infection due to the compromised competence of the immune system caused by this type of therapy.

Similarly, graft versus host disease (GVHD) is a complication that can occur after a stem cell or bone marrow transplant in which the newly transplanted material attacks the transplant recipient's body. The differences between the donor's cells and recipient's tissues often cause T-cells from the donor to recognize the recipient's body tissues as foreign, thereby causing the newly transplanted cells to attack the recipient. GVHD may complicate stem cell or bone marrow transplantation, thereby potentially limiting these life-saving therapies. Therefore, after a transplant, the recipient is usually administered a drug that suppresses the immune system, which helps reduce the chances or severity of GVHD. See Dugdale, David C., et al. "Graft-Versus-Host Disease," *MedlinePlus A.D.A.M Medical Encyclopedia*, Updated Jun. 2, 2010.

Autoimmune diseases, including rheumatoid arthritis (RA) and progressive systemic sclerosis (PSS), can be characterized by an overactive immune system which mistakes the body's own tissues as being a foreign substance. As a result, the body makes autoantibodies that attack normal cells and tissues. At the same time, regulatory T-cells, which normally function to regulate the immune system and suppress excessive reactions or autoimmunity, fail in this capacity. This may lead to, among other things, joint destruction in RA and inflammation of the connective tissue in PSS.

Where existing therapies for treating one or more diseases may result in certain unintended side effects, additional treatment may be desired or required. One known procedure which has been shown to be effective in the treatment of diseases and/or the side effects of existing therapies is extracorporeal photopheresis or "ECP". Extracorporeal photopheresis (also sometimes referred to as extracorporeal photochemotherapy) is a process that includes: (1) collection of mononuclear cells "MNC" from a patient, (2) photoactivation treatment of the collected mononuclear cells, and (3) reinfusion of the treated mononuclear cells back to the patient. More specifically, ECP involves the extracorporeal exposure of peripheral blood mononuclear cells combined with a photoactive compound, such as 8-methoxypsoralen or "8-MOP" which is then photoactivated by ultraviolet light, followed by the reinfusion of the treated mononuclear cells. It is believed that the combination of 8-MOP and UV radiation encourages and/or causes apoptosis or programmed cell death (also referred to herein as the "apoptosis trend") of ECP-treated cells.

Although the precise mechanism of action in ECP treatment (in the different disease states) is not fully known, according to early theories, it was believed that photoactivation causes 8-MOP to irreversibly covalently bind to the DNA strands contained in the T-cell nucleus. When the photochemically damaged T-cells are reinfused, cytotoxic effects are induced. For example, a cytotoxic T-cell or "CD8+ cell" releases cytotoxins when exposed to infected or damaged cells or otherwise attacks cells carrying certain foreign or abnormal molecules on their surfaces. The cytotoxins target the damaged cell's membrane and enter the target cell, which eventually leads to apoptosis or programmed cell death of the targeted cell. In other words, after the treated mononuclear cells are returned to the body, the immune system recognizes the dying abnormal cells and begins to produce healthy lymphocytes (T-cells) to fight against those cells.

In addition to the above, it has also been theorized that extracorporeal photopheresis also induces monocytes (a type of mononuclear cell) to differentiate into dendritic cells capable of phagocytosing and processing the apoptotic T-cell antigens. When these activated dendritic cells are re-infused into systemic circulation, they may cause a systemic cytotoxic CD8+ T-lymphocyte-mediated immune response to the processed apoptotic T-cell antigens like that described above. It will be appreciated that other possible mechanisms of action may be involved in achieving the benefits that have been observed from the ECP treatment of mononuclear cells and the subsequent benefits to patients undergoing ECP based therapies.

More recently, it has been postulated that ECP may result in an immune tolerant response in the patient. For example, in the case of graft versus-host disease, the infusion of apoptotic cells may stimulate regulatory T-cell generation, inhibit inflammatory cytokine production, cause the deletion of effective T-cells and result in other responses. See Peritt, "Potential Mechanisms of Photopheresis in Hematopoietic Stem Cell Transplantation," *Biology of Blood and Marrow Transplantation* 12:7-12(2006). While presently the theory of an immune tolerant response appears to be among the leading explanations, there exist other theories as to the mechanism of action of ECP relative to graft-versus-host disease, as well as other disease states.

In any event, it will be appreciated that ECP treatment directly promotes and encourages apoptosis of lymphocytes following exposure to UV light. Regardless of the precise mechanism of action, it is presently understood that apoptosis plays a role in the therapeutic properties achieved, and beneficial clinical effects of, ECP treatment.

Currently, known ECP treatment procedures (i.e. the apheresis collection of a mononuclear cell product from a patient, the addition of 8-MOP to the collected cell product, subsequent UV irradiation and the reinfusion of the treated mononuclear cell product) may be performed on two or more consecutive days on a weekly basis, the frequency depending on the state of the particular disease being treated and/or the patient's response to the treatment. Systems for performing ECP include, for example, the Cellex Photopheresis System developed by Therakos, Inc., of Exton, Pa. Further details of the Therakos system can be found, for example, in U.S. Pat. No. 5,984,887.

While the clinical benefits of ECP have been recognized, the use of ECP may be limited by logistical difficulties, including the need to repeatedly perform apheresis collections of mononuclear cells. Methods to avoid repeated MNC collection procedures have included collecting in a single apheresis procedure multiple therapeutic doses of MNCs performing ECP, with a single dose of MNCs being contemporaneously treated by ECP and returned to the patient, and cryopreserving the remaining untreated MNCs for later ECP treatment. See, for example, Merlin, E., et al. "Cryopreservation of mononuclear cells before extracorporeal photochemotherapy does not impair their anti-proliferative capabilities." *Cytotherapy* 2011; 13:248-255).

The cryopreservation of substantially all, or a portion of, mononuclear cell products derived from an extracorporeal photopheresis treatment, without significantly affecting the apoptosis trend of lymphocytes and/or other therapeutic properties or clinical benefits of ECP-based therapy after cryopreservation and the subsequent thawing, is described in U.S. Ser. No. 13/760,774, which is been incorporated by reference herein in its entirety. In this application, which was published as US 2013/0252227, the disclosed apparatus and methods multiple portions of ECP treated mononuclear cell products are collected from a single apheresis and photopheresis session, and are divided into smaller portions for subsequent administration, thus saving a patient from the burden of undergoing multiple or additional apheresis collections and relieving the clinician from having to repeat the ECP treatment procedure each time cryopreserved untreated mononuclear cell products are thawed.

By way of the present disclosure, an apparatus and method for the batch photoactivation of MNCs is described that also results in two or more therapeutic quantities of ECP-treated MNCs to result from a single collection procedure. The therapeutic quantities of MNCs produced by the apparatus and method may be reinfused to the patient directly after photoactivation, or preserved for future reinfusion by means including cryopreservation.

SUMMARY

In a first aspect, the present application is directed to a method for the batch photoactivation of mononuclear cells (MNCs) comprising: separating whole blood in a first collection cycle to obtain a first quantity of MNCs; separating whole blood in a second collection cycle to obtain a second quantity of MNCs while simultaneously photoactivating the first quantity of MNCs to obtain a first quantity of treated MNCs; either storing the first quantity of treated MNCs or reinfusing the first quantity of treated MNCs; photoactivating the second quantity of MNCs to obtain a second quantity of treated MNCs; either storing the second quantity of treated MNCs or reinfusing the second quantity of treated MNCs; and reinfusing any blood components remaining after the second collection cycle.

In a second aspect, the method is performed with a blood separation system including a disposable fluid circuit having a separation chamber, and the first collection cycle comprises: i) withdrawing whole blood from a patient; ii) priming the fluid circuit with whole blood; iii) introducing additional whole blood into the separation chamber for separation into plasma, RBCs and MNCs; iv) transferring a portion of the plasma to a first (plasma) container; v) sequestering the MNCs in a region of the separation chamber to obtain the first quantity of MNCs; vi) transferring the RBCs to a second (RBC) container; vii) transferring the first quantity of MNCs to a third (treatment) container optionally with whole blood or by returning saline or a quantity of the RBCs from the second (RBC) container to the separation chamber to displace the first quantity of MNCs out of the separation chamber; viii) optionally purging the first quantity of MNCs into the third (treatment) container with saline or plasma from the first (plasma) container; ix) introducing saline into the third (treatment) container to achieve a target hematocrit and volume for the first quantity of MNCs; x) adding a photoactivation agent to the third (treatment) container; xi) exposing the third (treatment) container to UVA light to obtain the first quantity of treated MNCs; and xii) simultaneously with steps ix), x) and xi), commencing the second collection cycle.

In a third aspect, if the first quantity of treated MNCs is to be stored, the method further comprises: xiii) sealing the third (treatment) container; xiv) if a fourth (treatment) container is not preattached to the disposable fluid circuit, attaching a fourth (treatment) container to the disposable fluid circuit, and opening a clamp to permit fluid flow to the fourth (treatment) container xv) commencing the second collection cycle by withdrawing a further whole blood from the patient; xvi) introducing whole blood into the separation chamber for separation into plasma, RBCs and MNCs; xvii) sequestering the MNCs in a region of the separation chamber to obtain the second quantity of MNCs; xviii) transferring the RBCs to the second (RBC) container; xix) transferring the second quantity of MNCs to the fourth (treatment) container optionally with whole blood or by returning saline or a quantity of the RBCs from the second (RBC) container to the separation chamber to displace the second quantity of MNCs out of the separation chamber; xx) optionally purging the second quantity of MNCs into the fourth (treatment) container with saline or plasma from the first (plasma) container; and xxi) introducing saline into the fourth (treatment) container to achieve a target hematocrit and volume for the second quantity of MNCs.

In a fourth aspect, if the first quantity of treated MNCs is to be reinfused during the second collection cycle, the method further comprises: xiii) commencing the second collection cycle by withdrawing a further whole blood from the patient; xiv) introducing whole blood into the separation chamber for separation into plasma, RBCs and MNCs; xv) sequestering the MNCs in a region of the separation chamber to obtain the second quantity of MNCs; xvi) transferring the RBCs to the second (RBC) container; xvii) transferring the second quantity of MNCs to the first (plasma) container optionally with whole blood or by returning saline or a quantity of the RBCs from the second (RBC) container to the separation chamber to displace the second quantity of MNCs out of the separation chamber; xviii) optionally purging the second quantity of MNCs into the first (plasma) container with saline or plasma; xix) reinfusing the first quantity of treated MNCs from the third (treatment) container; xx) transferring the second quantity of MNCs from the first (plasma) container into the third (treatment) container; and xxi) introducing saline into the third (treatment) container to achieve a target hematocrit and volume for the second quantity of MNCs.

In a fifth aspect, if the second quantity of treated MNCs is to be reinfused, the method further comprises: xxii) adding photoactivation agent to the third (treatment) container; xxiii) exposing the third (treatment) container to UVA light to obtain the second quantity of treated MNCs; xxiv) reinfusing the second quantity of treated MNCs and any blood components remaining in the fluid circuit after the second collection cycle; and xxv) disconnecting the patient from the fluid circuit.

In a sixth aspect, if the second quantity of treated MNCs is to be stored, the method further comprises: xxii) reinfusing any blood components remaining in the fluid circuit after the second collection cycle; xxiii) disconnecting the patient from the fluid circuit; xxiv) adding photoactivation agent to the third (treatment) container; xxv) exposing the third (treatment) container to UVA light to obtain the second quantity of treated MNCs; and xxvi) storing the second quantity of treated MNCs In a seventh aspect, related to the second aspect, the method may further comprise: after step vii), segregating any MNCs remaining in the fluid circuit and transferring the remaining MNCs to the third (treatment) container with an RBC push and plasma purge.

In an eighth aspect, related to the third aspect, the method may further comprise: after step xx), segregating any MNCs remaining in the fluid circuit and transferring the remaining MNCs to the fourth (treatment) container with an RBC push and plasma purge.

In a ninth aspect, related to the fourth aspect, the method may further comprise: after step xxiii), segregating any MNCs remaining in the fluid circuit and transferring the remaining MNCs to the third (treatment) container with an RBC push and plasma purge.

In a tenth aspect a system for performing batch photoactivation of MNCs is provided in which the system comprises a disposable fluid circuit and a reusable hardware component including a programmable controller configured to automatically operate the system in accordance with the methods set forth above.

DESCRIPTION OF THE ILLUSTRATED EMBODIMENTS

The subject matter of the present disclosure relates generally to apparatus and methods for providing multiple therapeutic quantities of mononuclear cell products treated by extracorporeal photopheresis (ECP) from a single apheresis or collection procedure. One dose of the treated MNCs may be contemporaneously reinfused to the patient, while the other doses of treated MNCs are saved for later reinfusion.

Turning now to one embodiment of the apparatus and methods described herein, mononuclear cells are provided. As used herein, "mononuclear cells" may also be referred to as "mononuclear cell product" or "MNC product". This may be accomplished by withdrawing whole blood from a patient, such as by an intravenous line or the like, and separating a mononuclear cell product from the whole blood by automated apheresis, centrifugation or other known automated or manual separation techniques. The mononuclear cell product may also be obtained from previously collected blood stored in a package, container or bag.

With regard to apheresis, the device in which the separation of blood occurs may include a centrifuge to provide a cell product comprising at least white blood cells. Non-limiting examples of apheresis devices that may be used to separate mononuclear cells from blood include the Alyx Separator and the Amicus® Separator made and sold by Fenwal, Inc. of Lake Zurich, Ill. One example of an apparatus and method of collecting mononuclear cells is provided in U.S. Pat. No. 6,027,657 which is incorporated by reference herein. With regard to manual collection, whole blood may be collected in a bag or container and separated, such as by centrifugation, into its various component parts, including, for example, red blood cells, plasma (which may or may not contain platelets) and white blood cells. White blood cells may be retained in the bag while the remaining blood components can be manually expressed from the bag such as by squeezing or manipulation of the bag. It will be appreciated that white blood cells may also be obtained by bone marrow processing and/or from cord blood.

Figure 1:
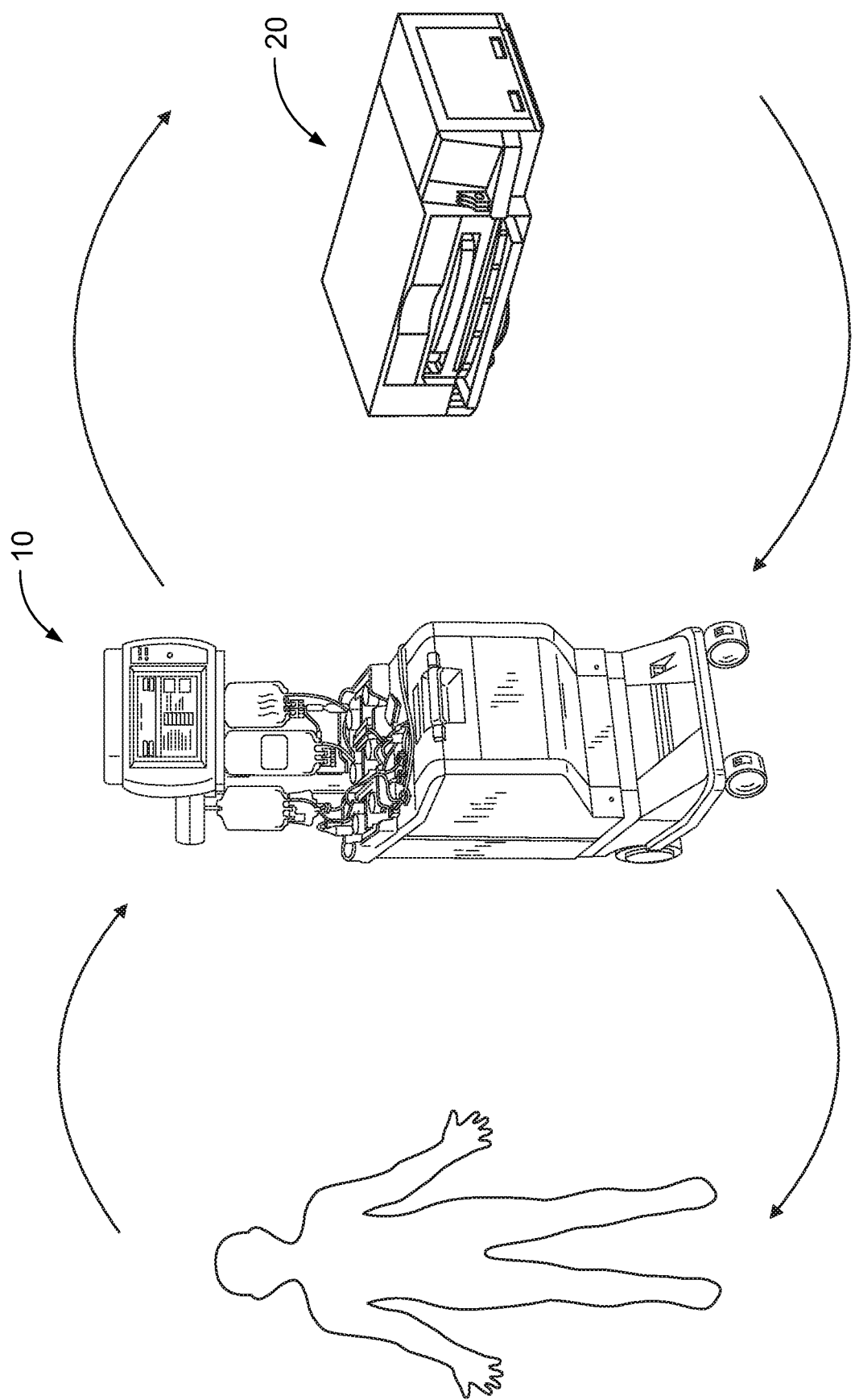
FIG. 1 is a diagram generally showing the mechanical components of an extracorporeal photopheresis treatment as described herein.

FIG. 1 shows, in general, the mechanical components that make up the exemplary apparatus and that are used in the methods described herein. In accordance with the present disclosure, the apparatus preferably includes a separation component 10 and a treatment (i.e., irradiation) component 20. A patient (or a container of previously-collected whole blood) is connected to separation component 10 via a blood processing set, i.e., fluid circuit 200. With reference to FIG. 1, whole blood is withdrawn from the patient (or from the container of previously-collected whole blood) and introduced into the separation component 10 where the whole blood is separated to provide a target cell population. In a preferred embodiment in accordance with the present disclosure, the target cell population may be a mononuclear cell product. Other components separated from the whole blood, such as red blood cells and platelets may be returned to the patient or collected in pre-attached containers of the blood processing set 200 for storage or further processing.

Figure 2:
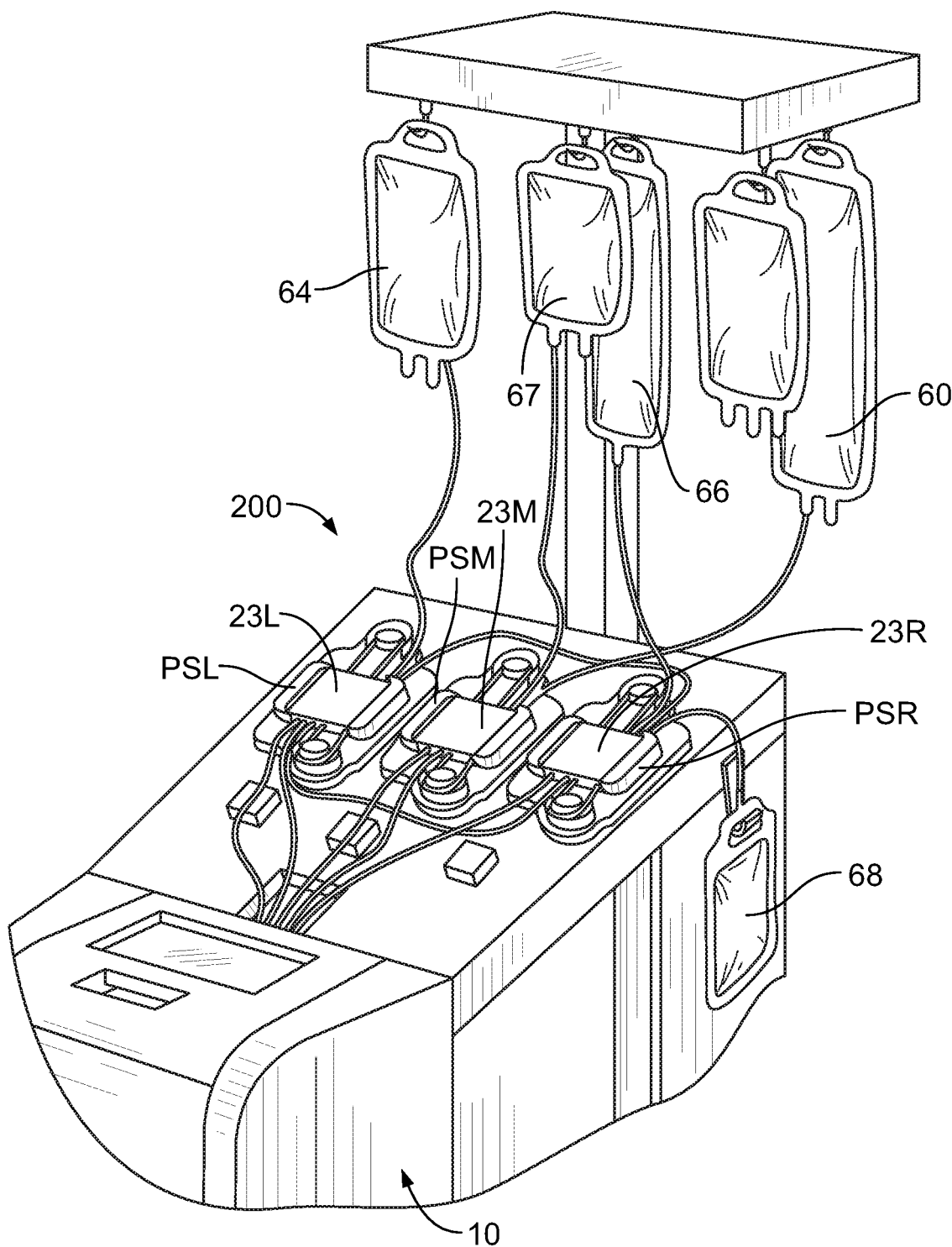
FIG. 2 is a partial perspective view of a separator useful in the methods and apparatus described herein.

Briefly, FIG. 2 shows a representative blood centrifuge 10 with fluid circuit 200 mounted thereon. The fluid circuit, shown in greater detail in FIG. 3, includes a blood processing container 14 defining a separation chamber 12 suitable for harvesting a mononuclear cell product from whole blood. As shown in FIG. 2, the disposable processing set or fluid circuit 200 is mounted on the front panel of separation component 10. In the present example, the separation component 10 includes a centrifugal separator (not shown) that holds the blood processing container 14. The processing set/fluid circuit 200 further includes a plurality of processing cassettes 23L, 23M and 23R, each having tubing loops for association with peristaltic pumps PSL, PSM and PSR, respectively on separation component 10.

Figure 3:
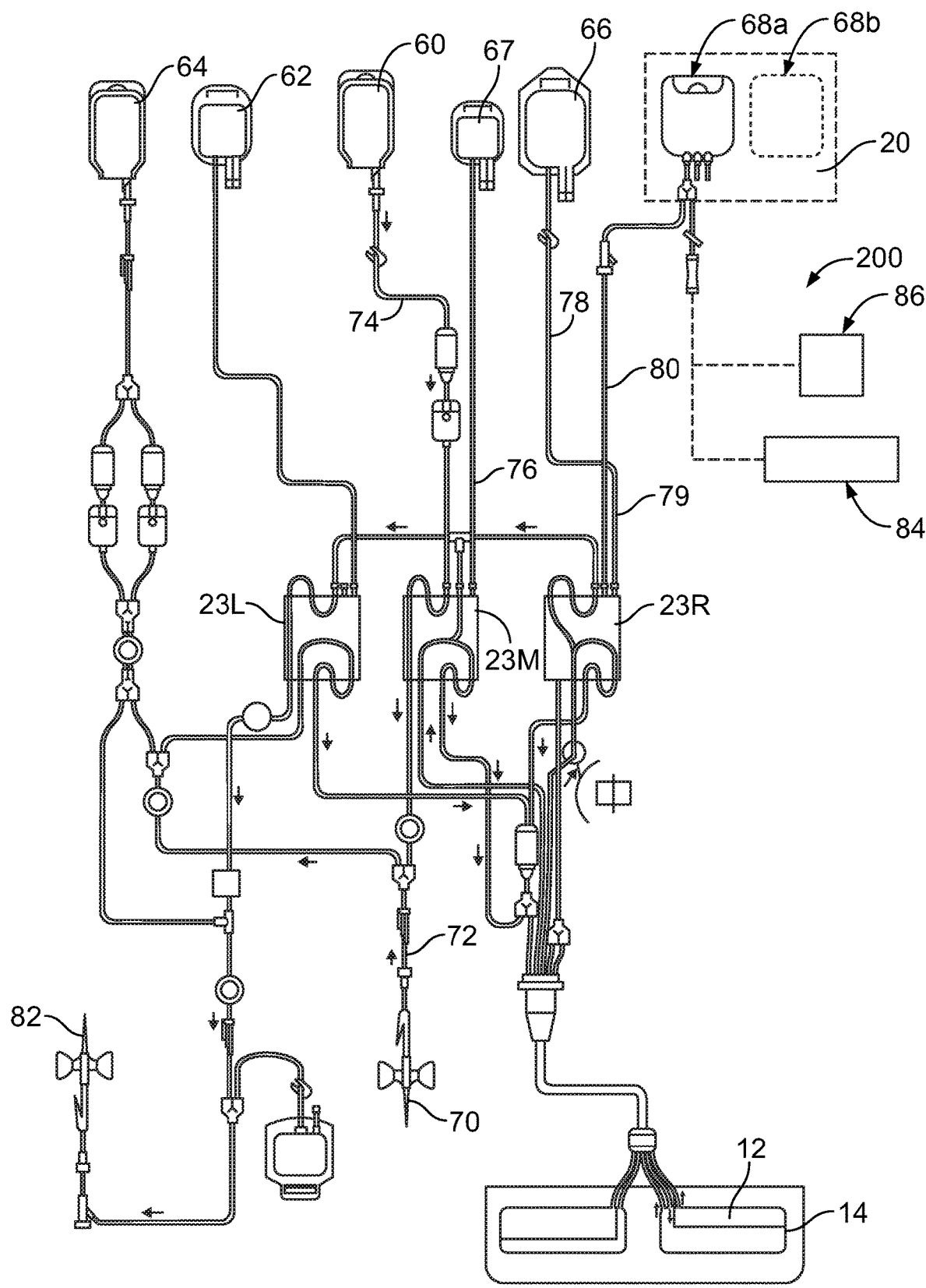
FIG. 3 is a diagram of the fluid circuit useful in the collection, treatment and cryopreservation of mononuclear cells as described herein.

Fluid circuit 200 also includes a network of tubing and pre-connected containers for establishing flow communication with the patient and for processing and collecting fluids and blood and blood components. As best seen in FIG. 3, disposable processing set 200 may include a container 60 for supplying anticoagulant (AC), a waste container 62 for collecting waste from one or more steps in the process for treating and washing mononuclear cells, a container 64 for holding saline or other wash or resuspension medium, a container 66 for collecting plasma, a container 67 for collecting red blood cells (RBCs) and one or more container (s) 68a, 68b for collecting and photoactivating the mononuclear cells (MNCs). As illustrated container 68a is preattached to the disposable fluid circuit, while container 68b is not. However, the second container 68b may also be preattached to the fluid circuit. Additional containers may be provided, for example, including a container 84 for holding a cryopreservation medium and/or a container 86 for holding a photoactive compound such as 8-MOP. Such containers may be integral with the fluid circuit 200 or provided separately.

With reference to FIG. 3, fluid circuit includes inlet line 72, an anticoagulant (AC) line 74 for delivering AC from container 60, an RBC line 76 for conveying red blood cells from separation chamber 12 of container 14 to container 67, a platelet-poor plasma (PPP) line 78 for conveying PPP to container 66 and line 80 for conveying mononuclear cells to and from separation chamber 12 and one of the containers 68a, 68b. As will be known to those skilled in the art, the blood processing set includes one or more venipuncture needle(s) for accessing the circulatory system of the patient. As shown in FIG. 3, fluid circuit 200 includes inlet needle 70 and return needle 82. In an alternative embodiment, a single needle can serve as both the inlet and outlet needle.

Fluid flow through fluid circuit 200 is preferably driven, controlled and adjusted by one or more microprocessor-based controllers in cooperation with the valves, pumps, weight scales and sensors of device 10 and fluid circuit 200, the details of which are described in the previously mentioned U.S. Pat. No. 6,027,657. In one embodiment, the controller can be programmed to control various operations performed by the apparatus or device 10 disclosed herein. For example, the controller may be programmed to separate mononuclear cells from whole blood within the separation chamber 12 of the fluid circuit 200, combine the separated mononuclear cell product with a photoactive compound, and irradiate mononuclear cell product with ultraviolet light in photoactivation device 20 (which device may be associated with separation component 10 or separately provided therefrom). It will be appreciated that the controller may also be programmed to perform additional processing and treatment steps as necessary or desired.

Collection of the mononuclear cell product may proceed in one or more cycles. The number of processing cycles conducted in a given therapeutic procedure will depend upon the total desired amount or portion of MNC to be collected. For example, in a representative procedure, two collection cycles may be performed sequentially. During the two cycles, about 500-4000 ml of total whole blood can be processed, obtaining a MNC product volume of about 15 ml per cycle and a total volume of 30 ml of MNC product. The final volume of collected mononuclear cell product is then provided for further treatment in accordance with the present disclosure. Of course, the collection of the MNC product is not limited to the method described above. MNCs may be collected in any manner known to those of skill in the art.

Effective treatment of the mononuclear cell product with light may require that the amount of collected mononuclear cells have a suitable hematocrit. Thus, it may be desired or even necessary to dilute the mononuclear cell product with a diluting solution such as plasma or saline. In the example described above, approximately 30 ml of MNC product may be diluted in an amount of saline having a volume of about 1-300 ml and more preferably about 170 ml of saline.

The diluted mononuclear cell product (in container 68a or 68b) is then combined with the suitable photoactivation agent. As discussed above, for ECP treatment, the compound 8-methoxypsoralen (8-MOP) has been shown to be an effective photoactivation agent, however, other suitable photoactivation agents may be used, including, for example, a psoralen compound. It will be appreciated that the mononuclear cell product may be combined with a photosensitive compound in any amount effective for satisfactorily treating cells by ECP. In one example, 8-MOP is combined with the collected and diluted mononuclear cell product to arrive at a mixture having a final 8-MOP concentration of 200 nanograms/mL and/or any suitable effective amount. Typically, the mononuclear cell product may be combined with the photoactivation agent to arrive at a final 8-MOP concentration in a range of about 100 to 400 nanograms/mL.

The combination of 8-MOP and mononuclear cells can be accomplished by in vitro methods, such as by combining 8-MOP with a mononuclear cell product that has been collected by apheresis. In one example, the fluid circuit 200 (in which mononuclear cells are separated from whole blood) may include a source of 8-MOP in container 86. The 8-MOP or other photoactivation agent may be added directly to container 68 or added elsewhere into the fluid circuit 200, either manually by a syringe and/or under the direction of the microprocessor-based controller, which may be programmed to automatically deliver the desired amount of photoactive agent before, during, or after the MNC product collection, based on the volume of MNC product collected or to be collected. Alternatively, the desired volume of the agent may be pre-added to the container 68a or 68b.

The resulting combination of mononuclear cell product mixed with 8-MOP is preferably then exposed to or irradiated with light. As noted above, the mononuclear cell product collected in accordance with the collection process described above may be collected in container 68a or 68b that is suitable for irradiation by light of a selected wavelength. By "suitable" it is meant that the walls of the container are sufficiently transparent to light of the selected wavelength to activate the photoactive agent. In treatments using UVA light, for example, container walls made of ethylene vinyl acetate (EVA) are suitable.

Accordingly, container 68a or 68b in which the mononuclear cell product is collected may serve both as the collection container and the irradiation container. Container 68a or 68b may be placed inside irradiation device 20 by the operator or more preferably, may be placed inside the irradiation chamber of irradiation device 20 at the beginning of the ECP procedure and prior to whole blood withdrawal (as shown by the broken lines representing device 20 in FIG. 3). In any event, container 68a or 68b may remain integrally connected to the remainder of fluid circuit 200 during the entire procedure, thereby maintaining the closed or functionally closed condition of fluid circuit 200. Alternatively, container 68a or 68b may be disconnected after mononuclear cell collection has been completed but before 8-MOP is added to the mononuclear cell product in container 68a or 68b.

As noted above, the fluid circuit 200 is adapted for association with the treatment component (i.e., irradiation device) 20. It will also be appreciated, however, that the irradiation device does not have to be integral or even associated with the fluid circuit 200 and/or separation device 10. In fact, the irradiation device 20 may be in an entirely separate location from the separation device and/or circuit, such as a location in an entirely different room or building. In such a case, container 68a or 68b may be disconnected after collection has been completed for the later addition of 8-MOP to the mononuclear cell product in container 68 and/or irradiation of the container in one or more different locations.

One known apparatus suitable for the irradiation of mononuclear cells is available from sources such as Cerus Corporation, of Concord, Calif., such as, for example the irradiation device described in U.S. Pat. No. 7,433,030, the contents of which is likewise incorporated by reference herein in its entirety. As shown and described in U.S. Pat. No. 7,433,030, irradiation device 20 preferably includes a tray or other holder for receiving one or more containers during treatment. Other irradiation devices may also be suitable for use with the method and apparatus described herein. However, it is also contemplated that suitable irradiation may also be accomplished by any source of ultraviolet light which provides UV light at a selected UVA dose, including natural sunlight.

Regardless of the type of irradiation device and/or the source of UV light, the mononuclear cell product combined with photoactivation agent (8-MOP) is irradiated for a selected UVA dose. In one non-limiting example, during treatment, the mononuclear cell product may be exposed to UV bulbs having a UVA wavelength in the UVA range of about 320 nm to 400 nm for a selected period of time, such as approximately 10-60 minutes, resulting in an average UVA exposure of approximately 0.5-5.0 $J/cm^2$ and preferably approximately 1-2 $J/cm^2$ or even more preferably approximately 1.5 J/cm2 per lymphocyte. Following UV light exposure or irradiation of the mononuclear cell product combined with 8-MOP, the freshly treated cell product, or a portion thereof, may then be returned to the patient.

In keeping with the present application, a method for the batch activation of MNCs is set forth. In general, the method comprises two MNC collection cycles performed one after the other, with the MNC product from the first collection cycle being photoactivated while the second collection cycle is commenced. The treated MNCs from the first collection cycle are then either stored for later reinfusion or reinfused during the second collection cycle. At the end of the second collection cycle, the collected MNCs are again either stored or reinfused. If reinfused, photoactivation is performed and the treated cells along with the blood components remaining in the kit (primarily plasma and RBCs) are reinfused to the patient. If the collected MNCs from the second collection cycle are to be stored, the blood components remaining in the kit are reinfused and the patient disconnected from the system. The MNCs from the second collection cycle are then photoactivated and stored for later reinfusion. As noted in U.S. Ser. No. 13/760,774, the treated MNCs may be cryopreserved.

Figure 4:
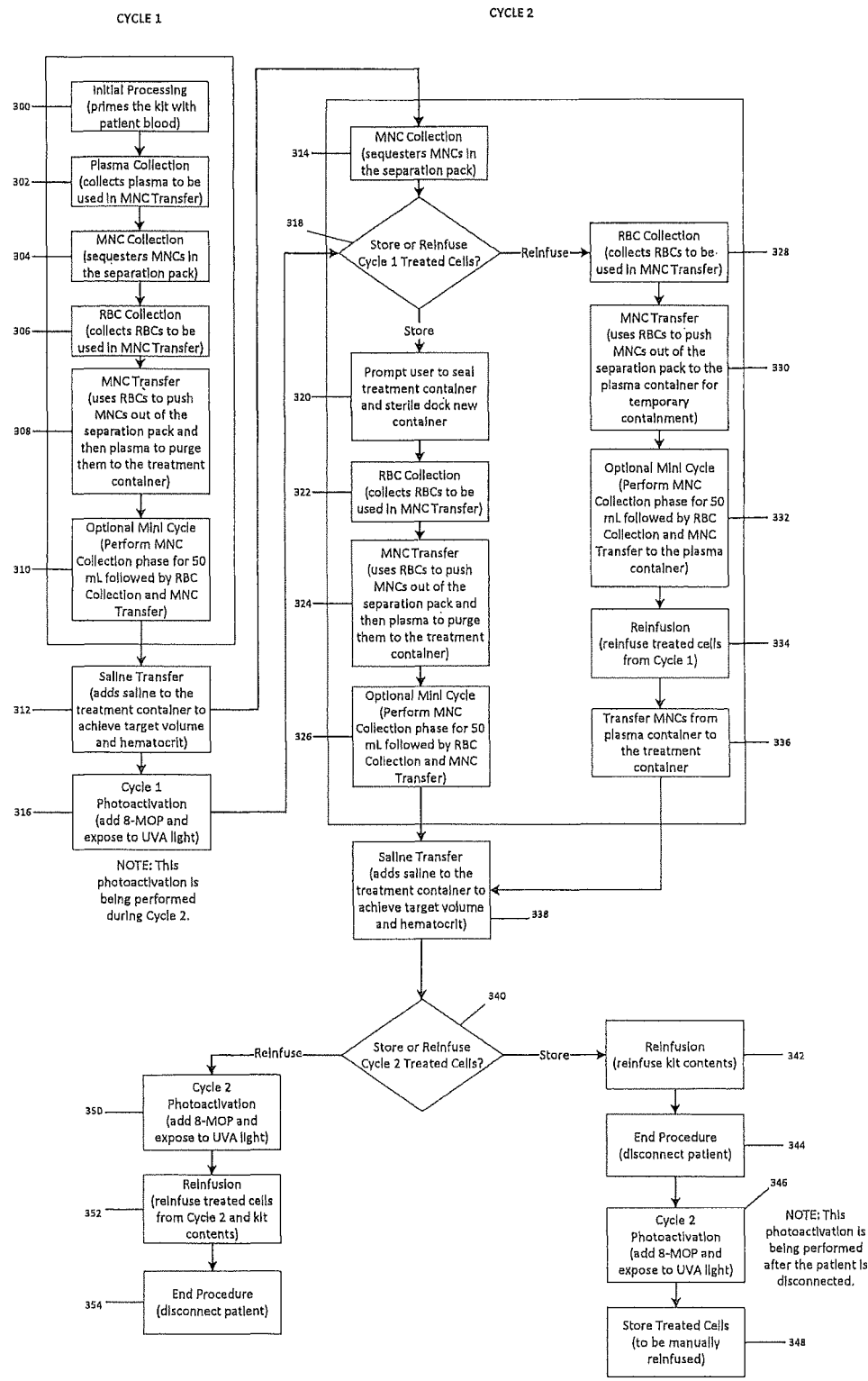
FIG. 4 is a flow chart setting forth the steps of a method of batch photoactivation according to the present application.

With reference to FIG. 4, a flow chart is seen that more specifically sets forth the steps of a representative a MNC batch processing method having a first cycle ("Cycle 1") and a second cycle ("Cycle 2") that are performed consecutively. Cycle 1 commences with an initial step (Step 300) in which whole blood is withdrawn from the patient and used for priming the fluid circuit 200 prior to separation of the whole blood into its components. Upon completion of priming, additional whole blood is introduced into the separation chamber 12 for separation into plasma, RBC and MNC components.

A quantity of plasma is separated from the whole blood (Step 302) and is transferred to the plasma container 66, and may be later used in the transfer of MNCs from the separation chamber 12 to the MNC collection/treatment container 68a. MNCs are then separated and sequestered in a region of the separation chamber 12 (Step 304). RBCs are separated (Box 306) and collected in container 67, also potentially for later use in the transfer of MNCs from the separation chamber 12 to the MNC collection/treatment container 68a.

The separated MNCs are then transferred to the collection/treatment container 68a (Step 308). This may be accomplished by returning a quantity of the separated RBCs from the collection container 67 back to the separation chamber 12 to push the separated MNCs out of the separation chamber 12. Alternatively, saline could be used for this purpose. A further alternative would be to block the packed RBC outlet port of the separation chamber 12 and continue to introduce whole blood into the separation chamber to push the MNCs out through the plasma line and into container 68a. While the MNCs transferred to the collection container may include some residual RBCs, the amount of residual RBC is preferably such that the final hematocrit of the suspension of MNCs in the collection/treatment container after dilution is in the range of 2%-3%. A hematocrit detector may be used to control the amount of residual red blood cells flowing to the collection/treatment container 68a during the transfer. Once the transfer of MNCs to the collection/treatment container resulting from the RBC push is completed, plasma from collection container 66 may be used to purge the MNCs into the collection/treatment container 68a. Alternatively, saline may also be used for this purpose Optionally, a "mini" MNC collection cycle may be performed (Step 310) to segregate and collect whatever MNCs that might still reside in the separation chamber as part of a collection efficiency step. The additional MNCs segregated by the mini cycle are then transferred to the collection/treatment container 68a with an RBC push and plasma purge, as described above.

Saline is then transferred from the container 64 to the collection/treatment container 68a (Step 312) to achieve a targeted volume and hematocrit for the suspension of MNCs in the container 68a. Cycle 2 is then commenced with further blood being withdrawn from the patient and is introduced into the separation chamber 12 for separation into plasma, RBC and MNC components, with the MNCs being separated and sequestered in a region of the separation chamber 12 (Step 314). Concurrently, a photoactivation agent (e.g., 8-MOP) is added to MNC suspension in the collection/treatment container 68*a* and the container 68*a* is then exposed to UVA light (Step 316), so that the container 68*a* now contains treated MNCs.

As noted above, the treated MNCs from the first collection cycle are then either stored for later reinfusion or reinfused during the second collection cycle (Step 318). If the treated cells from the first cycle are to be stored, the collection/treatment container 68*a* is sealed. Then, if the collection/treatment container 68*b* is not preattached to the disposable fluid circuit, a new collection/treatment container 68*b* may be connected to the kit 200 by sterile docking (Step 320), and access to the container being provided by opening a clamp on line 80.

RBCs are separated (Step 322) and collected in container 67, again potentially for use in the transfer of MNCs from the second collection cycle from the separation chamber 12 to the MNC collection/treatment container 68*a*. The separated MNCs (from Step 314) are then transferred to the new collection/treatment container (Step 324). As described above, this may be accomplished by returning a quantity of the separated RBCs (from Step 320) from the collection container 67 back to the separation chamber 12 to push the separated MNCs out of the separation chamber 12, as described above. Alternatively, saline could be used for this purpose. A further alternative, as described above, would be to block the packed RBC outlet port of the separation chamber 12 and continue to introduce whole blood into the separation chamber to push the MNCs out through the plasma line and into container 68*b*. Plasma from collection container 66 collected during the first collection cycle is then used to purge the MNCs into the collection/treatment container 68*b*. Alternatively, saline also could be used for this purpose.

Again an optional mini MNC collection cycle may be performed (Step 326) to segregate and collect whatever MNCs that might still reside in the separation chamber, with the additional MNCs segregated by the mini cycle then being transferred to the collection/treatment container 68*b* with an RBC push and plasma purge, as described above.

If the treated cells from the first collection cycle are to be reinfused, RBCs are separated (Step 328) and collected in container 67, again for use in the transfer of MNCs from the second collection cycle from the separation chamber 12 to an in-process container. The separated MNCs are then transferred to an in-process container for temporary storage (Step 330) by returning a quantity of the separated RBCs from the collection container 67 back to the separation chamber 12 to push the separated MNCs out of the separation chamber 12. The in-process container may be the container 66 which previously was used for storage of plasma.

An optional mini MNC collection cycle may be performed (Step 332) to segregate and collect whatever MNCs that might still reside in the separation chamber, with the additional MNCs segregated by the mini cycle then being transferred to the in process/plasma container 66 with an RBC push.

The treated MNCs from the first collection cycle are then reinfused from the collection/treatment container 68*a* to the patient (Step 334). The MNCs in the in process/plasma container 66 are then transferred to the collection/treatment container 68*a* (Step 336), to which saline is added to achieve a target volume and hematocrit (Step 338).

As noted above, at the end of the second collection cycle, the collected MNCs in the second collection cycle are either stored or reinfused (Step 340). If the treated cells from the second cycle are to be stored, the contents of the kit are reinfused into the patient (Step 342), and the patient disconnected from the kit (Step 344). Photoactivation agent is added to MNC suspension in the collection/treatment container 68*a* and the container 68*a* is then exposed to UVA light (Step 346). The treated cells are then stored for future reinfusion (Step 348). As noted above, the treated MNCs may be cryopreserved, as described in U.S. Ser. No. 13/760,774.

If the treated cells from the second cycle are to be reinfused, photoactivation agent (e.g., 8-MOP) is added to MNC suspension in the collection/treatment container 68*a* and the container 68*a* is then exposed to UVA light (Step 350). The treated cells from the second collection cycle are then reinfused into the patient, along with the contents of the kit (Step 352), and the patient disconnected from the kit to end the procedure (Step 354).

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description.

We claim:

1. A method for the batch photoactivation of mononuclear cells (MNCs) wherein the method is performed with a blood separation system including a disposable fluid circuit having a separation chamber, the method comprising:
  a) separating whole blood in a first collection cycle to obtain a first quantity of MNCs, wherein the first collection cycle comprises
   i) withdrawing whole blood from a patient;
   ii) priming the disposable fluid circuit with whole blood;
   iii) introducing additional whole blood into the separation chamber for separation into plasma, RBCs and MNCs;
   iv) transferring a portion of the plasma to a first (plasma) container;
   v) sequestering the MNCs in a region of the separation chamber to obtain the first quantity of MNCs;
   vi) transferring the RBCs to a second (RBC) container;
   vii) transferring the first quantity of MNCs to a third (treatment) container by displacing the first quantity of MNCs out of the separation chamber with either saline, RBCs or whole blood;
   viii) purging the first quantity of MNCs into the third (treatment) container with either saline or plasma from the first (plasma) container;
   ix) introducing saline into the third (treatment) container to achieve a target hematocrit and volume for the first quantity of MNCs;
   x) adding a photoactivation agent to the third (treatment) container;
   xi) exposing the third (treatment) container to UVA light to obtain the first quantity of treated MNCs; and
   xii) simultaneously with steps ix), x) and xi), commencing a second collection cycle;
  b) separating whole blood in the second collection cycle to obtain a second quantity of MNCs while simultaneously photoactivating the first quantity of MNCs to obtain the first quantity of treated MNCs;

c) either storing the first quantity of treated MNCs or reinfusing the first quantity of treated MNCs;
d) photoactivating the second quantity of MNCs to obtain a second quantity of treated MNCs;
e) either storing the second quantity of treated MNCs or reinfusing the second quantity of treated MNCs; and
f) reinfusing any blood components remaining after the second collection cycle.

2. The method of claim 1 in which the first quantity of treated MNCs is stored, further comprising: xiii) sealing the third (treatment) container; xiv) if not preattached, attaching a fourth (treatment) container to the disposable fluid circuit; xv) commencing the second collection cycle by withdrawing a further whole blood from the patient; xvi) introducing whole blood into the separation chamber for separation into plasma, RBCs and MNCs; xvii) sequestering the MNCs in a region of the separation chamber to obtain the second quantity of MNCs; xviii) transferring the RBCs to the second (RBC) container; xix) transferring the second quantity of MNCs to the fourth (treatment) container by displacing the second quantity of MNCs out of the separation chamber with either saline, RBCs or whole blood; xx) purging the second quantity of MNCs into the fourth (treatment) container with either saline or plasma from the first (plasma) container; and xxi) introducing saline into the fourth (treatment) container to achieve a target hematocrit and volume for the second quantity of MNCs.

3. The method of claim 2 further comprising: after step xx), segregating any MNCs remaining in the fluid circuit and transferring the remaining MNCs to the fourth (treatment) container with an RBC push and plasma purge.

4. The method of claim 1 in which the first quantity of treated MNCs is reinfused during the second collection cycle, further comprising: xiii) commencing the second collection cycle by withdrawing a further whole blood from the patient; xiv) introducing whole blood into the separation chamber for separation into plasma, RBCs and MNCs; xv) sequestering the MNCs in a region of the separation chamber to obtain the second quantity of MNCs; xvi) transferring the RBCs to the second (RBC) container; xvii) transferring the second quantity of MNCs to the first (plasma) container by displacing the second quantity of MNCs out of the separation chamber with either saline, RBCs or whole blood; xviii) purging the second quantity of MNCs into the first (plasma) container with either saline or plasma; xix) reinfusing the first quantity of treated MNCs from the third (treatment) container; xx) transferring the second quantity of MNCs from the first (plasma) container into the third (treatment) container; and xxi) introducing saline into the third (treatment) container to achieve a target hematocrit and volume for the second quantity of MNCs.

5. The method of claim 4 in which the second quantity of treated MNCs is to be reinfused, further comprising: xxii) adding photoactivation agent to the third (treatment) container; xxiii) exposing the third (treatment) container to UVA light to obtain the second quantity of treated MNCs; xxiv) reinfusing the second quantity of treated MNCs and any blood components remaining in the fluid circuit after the second collection cycle; and xxv) disconnecting the patient from the fluid circuit.

6. The method of claim 4 in which the second quantity of treated MNCs is to be stored, further comprising: xxii) reinfusing any blood components remaining in the fluid circuit after the second collection cycle, xxiii) adding photoactivation agent to the third (treatment) container; xxiv) disconnecting the patient from the fluid circuit; xxv) adding photoactivation agent to the third (treatment) container; xxvi) exposing the third (treatment) container to UVA light to obtain the second quantity of treated MNCs, and xxvii) storing the second quantity of treated MNCs.

7. The method of claim 4 further comprising: after step xviii), segregating any MNCs remaining in the fluid circuit and transferring the remaining MNCs to the third (treatment) container with an RBC push and plasma purge.

8. The method of claim 1 further comprising: after step vii), segregating any MNCs remaining in the fluid circuit and transferring the remaining MNCs to the third (treatment) container with an RBC push and plasma purge.

9. A system for the batch photoactivation of mononuclear cells (MNCs) comprising:
a) a disposable fluid circuit comprising a separation chamber for separating whole blood into one or more components including MNCs, red blood cells (RBCs) and plasma, and first, second, third and fourth containers;
b) a durable hardware component including a separation device adapted to receive the separation chamber for effecting separation of MNCs from whole blood, and
c) a programmable controller configured to a) automatically separate whole blood in a first collection cycle to obtain a first quantity of MNCs, wherein the first collection cycle comprises:
i) withdrawing whole blood from a patient; ii) priming the fluid circuit with whole blood; iii) introducing additional whole blood into the separation chamber for separation into plasma, RBCs and MNCs; iv) transferring a portion of the plasma to the first (plasma) container; v) sequestering the MNCs in a region of the separation chamber to obtain the first quantity of MNCs; vi) transferring the RBCs to the second (RBC) container; vii) transferring the first quantity of MNCs to the third (treatment) container by displacing the first quantity of MNCs out of the separation chamber with either saline, RBCs or whole blood; viii) purging the first quantity of MNCs into the third (treatment) container with either saline or plasma from the first (plasma) container; ix) introducing saline into the third (treatment) container to achieve a target hematocrit and volume for the first quantity of MNCs; x) adding a photoactivation agent to the third (treatment) container; xi) exposing the third (treatment) container to UVA light to obtain the first quantity of treated MNCs; and xii) simultaneously with steps ix), x) and xi), commencing a second collection cycle; and
b) separate whole blood in the second collection cycle to obtain a second quantity of MNCs and simultaneously photoactivate the first quantity of MNCs to obtain a first quantity of treated MNCs, c) prompt an operator to select to store the first quantity of treated MNCs or to reinfuse the first quantity of treated MNCs, d) if reinfusion is selected, reinfuse the first quantity of treated MNCs, e) photoactivate the second quantity of MNCs to obtain a second quantity of treated MNCs, f) prompt an operator to select to store the second quantity of treated MNCs or to reinfuse the second quantity of treated MNCs, g) if reinfusion is selected, reinfuse the second quantity of treated MNCs, and h) reinfuse any blood components remaining in the disposable fluid circuit after the second collection cycle.

10. The system of claim 9 wherein, if the first quantity of treated MNCs is stored, the programmable controller is further configured to automatically operate the system to: xiii) prompt the operator to seal the third (treatment) container; xiv) if not preattached, prompt the operator to attach the fourth (treatment) container to the disposable fluid circuit; xv) commence the second collection cycle by withdrawing a further whole blood from the patient; xvi) introduce whole blood into the separation chamber for separation into plasma, RBCs and MNCs; xvii) sequester the MNCs in a region of the separation chamber to obtain the second quantity of MNCs; xviii) transfer the RBCs to the second (RBC) container; xix) transfer the second quantity of MNCs to the fourth (treatment) container by displacing the second quantity of MNCs out of the separation chamber with either saline, RBCs or whole blood; xx) purge the second quantity of MNCs into the fourth (treatment) container with saline or plasma from the first (plasma) container; and xxi) introduce saline into the fourth (treatment) container to achieve a target hematocrit and volume for the second quantity of MNCs.

11. The system of claim 9 wherein, if the first quantity of treated MNCs is reinfused, the programmable controller is further configured to automatically operate the system to: xiii) commence the second collection cycle by withdrawing a further whole blood from the patient; xiv) introduce whole blood into the separation chamber for separation into plasma, RBCs and MNCs; xv) sequester the MNCs in a region of the separation chamber to obtain the second quantity of MNCs; xvi) transfer the RBCs to the second (RBC) container; xvii) transfer the second quantity of MNCs to the first (plasma) container by displacing the second quantity of MNCs out of the separation chamber with either saline, RBCs or whole blood; xviii) purge the second quantity of MNCs into the first (plasma) container with saline or plasma; xix) reinfuse the first quantity of treated MNCs from the third (treatment) container; xx) transfer the second quantity of MNCs from the first (plasma) container into the third (treatment) container; and xxi) introduce saline into the third (treatment) container to achieve a target hematocrit and volume for the second quantity of MNCs.

12. The system of claim 11 wherein, if the second quantity of MNCs is to be reinfused, the programmable controller is further configured to automatically operate the system to: xxii) add photoactivation agent to the third (treatment) container; xxiii) expose the third (treatment) container to UVA light to obtain the second quantity of treated MNCs; xxiv) reinfuse the second quantity of treated MNCs and any blood components remaining in the fluid circuit after the second collection cycle; and xxv) prompt the operator to disconnect the patient from the fluid circuit.

13. The system of claim 11 wherein, if the second quantity of MNCs is to be stored, the programmable controller is further configured to automatically operate the system to: xxii) reinfuse any blood components remaining in the fluid circuit after the second collection cycle, xxiii) add photoactivation agent to the third (treatment) container; xxiii) prompt the operator to disconnect the patient from the fluid circuit; xxiv) add photoactivation agent to the third (treatment) container, and xxv) expose the third (treatment) container to UVA light to obtain the second quantity of treated MNCs.

* * * * *